United States Patent [19]

Bille et al.

[11] Patent Number: 5,439,462
[45] Date of Patent: Aug. 8, 1995

[54] APPARATUS FOR REMOVING CATARACTOUS MATERIAL

[75] Inventors: Josef F. Bille, Heidelberg, Germany; David Schanzlin, St. Louis, Mo.

[73] Assignee: Intelligent Surgical Lasers, San Diego, Calif.

[21] Appl. No.: 124,237

[22] Filed: Apr. 4, 1994

Related U.S. Application Data

[63] Continuation-in-part of Ser. No. 841,614, Feb. 25, 1992, Pat. No. 5,246,435.

[51] Int. Cl.$^6$ .............................................. A61B 17/36
[52] U.S. Cl. ........................................ 606/6; 606/4; 606/5
[58] Field of Search ................................... 606/10–12, 606/107, 4–6; 372/9, 10, 23, 24, 33

[56] References Cited

U.S. PATENT DOCUMENTS

| | | | |
|---|---|---|---|
| 3,710,798 | 1/1973 | Bredemeier | 606/11 |
| 3,971,382 | 7/1976 | Krasnov | |
| 4,309,998 | 1/1982 | Aron nee Rosa et al. | |
| 4,391,275 | 7/1983 | Frankhauser | |
| 4,538,608 | 8/1985 | L'Esperance, Jr. | 606/6 |
| 4,669,466 | 6/1987 | L'Esperance | |
| 4,764,930 | 8/1988 | Bille et al. | 372/23 |
| 5,049,147 | 9/1991 | Danon | 606/4 |
| 5,137,530 | 8/1992 | Sand | 606/5 |

FOREIGN PATENT DOCUMENTS

| | | | |
|---|---|---|---|
| 0224322 | 6/1987 | European Pat. Off. | 606/5 |
| 0280414 | 8/1988 | European Pat. Off. | 606/5 |

OTHER PUBLICATIONS

L'Esperance, Francis A. Jr. *Opthalmic Lasers, Photocoagulation, Photoradiation and Surgery.* Columbia University College of Physicians and Surgeons, N.Y, N.Y., Second Edition, 1983, pp. 529–538.

Primary Examiner—Stephen C. Pellegrino
Assistant Examiner—Michael Peffley
Attorney, Agent, or Firm—Nydegger & Associates

[57] ABSTRACT

An ophthalmic laser system is disclosed for removing cataractous tissue from the lens capsule of an eye by phacofragmentation of the lens tissue for subsequent aspiration of the treated tissue. More specifically, a cutting laser is provided which creates a plurality of computer controlled and directed incisions in various strata through the lens tissue. Within each stratum, each incision is computer controlled and is made in the direction from a posterior to an anterior position. The strata are stacked on each other in the posterior-anterior direction, and each includes a plurality of minute incisions. The most posterior stratum of incisions is created first by referencing the cutting laser back into the lens tissue from the posterior capsule. Subsequent, more anterior strata, are created by referencing the cutting layer from the tissue treated by the previous stratum of incisions. In each stratum, the vapors which result from the incisions infiltrate between the layers of the lens tissue fragmenting and liquefying the tissue. The computer controlled device can automatically determine locations and dimensions of incisions, as well as automatically adjusting incision curvature and beam intensity as the incision point is moved from stratum to stratum. After the device liquifies the lens tissue it can then be aspirated.

11 Claims, 2 Drawing Sheets

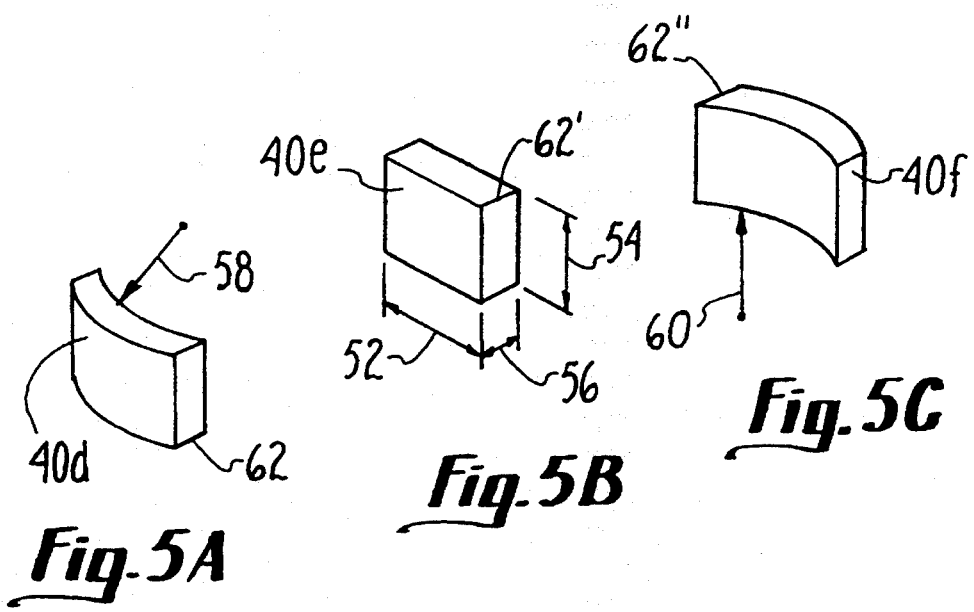
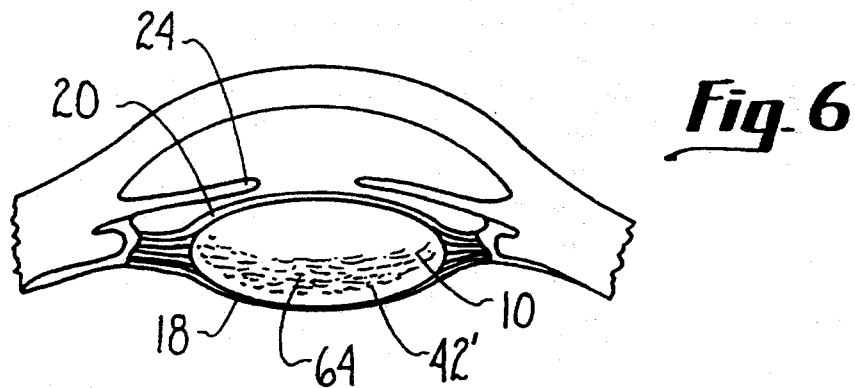
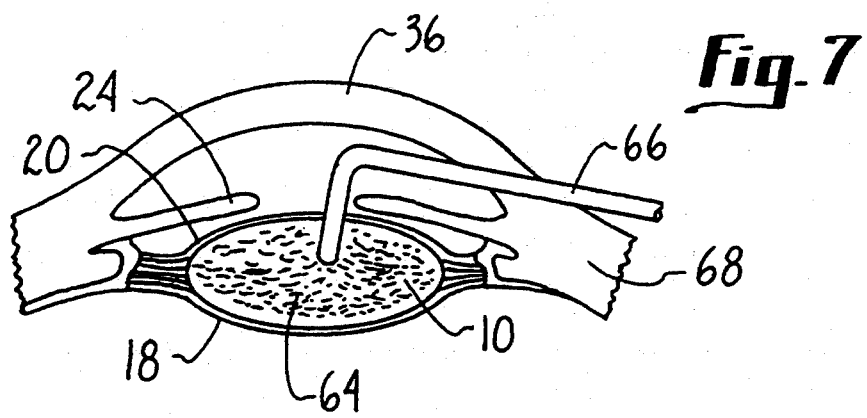

APPARATUS FOR REMOVING CATARACTOUS MATERIAL

This is a continuation-in-part of application Ser. No. 07/841,614 filed on Feb. 25, 1992, now U.S. Pat. No. 5,246,435.

FIELD OF THE INVENTION

The present invention pertains generally to ophthalmic surgical devices. More particularly, the present invention pertains to a device for generating a cutting beam of laser light to photoablate selected tissue of the eye. The present invention is particularly, but not exclusively useful for removing cataractous tissue from the lens capsule of an eye.

BACKGROUND OF THE INVENTION

Although cataracts originate from several different pathologies, their common manifestation is an opacity of the crystalline lens of the eye which either impairs or obstructs the vision of an afflicted individual. In any event, there are several well known cataract surgical procedures which can be performed to alleviate or eliminate the problem. The most radical of these procedures is a lentectomy. In a lentectomy, the opaque crystalline lens is effectively removed from the lens capsule. It is then replaced with an acrylic or plastic lens. Most commonly, the lentectomy is performed by using a knife to cut the lens out of the lens capsule. Recently, however, procedures have been suggested wherein laser energy is used to remove the cataractous tissue from the lens capsule.

U.S. Pat. No. 4,538,608 which issued to L'Esperance, Jr. for an invention entitled "Method and Apparatus for Removing Cataractous Lens Tissue by Laser Radiation" is an example of a device which employs laser energy to perform a lentectomy. According to the teachings of L'Esperance, laser energy is directed onto the anterior aspect of the cataractous lens tissue and the laser beam is then scanned within a limiting perimeter until the cataractous tissue has been photoablated. In accordance with this procedure, the cataractous tissue in the lens is removed in sheets from the anterior aspect of the lens toward the posterior capsule. An adverse consequence of this approach is that it is necessary to continually be working through a fragmented layer of lens tissue which scatters light and thereby causes unwanted inefficiencies.

The present invention, however, recognizes that the anatomy of the lens tissue in the eye, and the reaction of this tissue to photoablation, permits a procedure for removing cataractous tissue from the lens capsule which is quite different from the procedures suggested by L'Esperance. To appreciate this, it is first necessary to understand the anatomy which is being treated.

The lens of an eye is a transparent biconvex body of crystalline tissue which is situated between the posterior chamber and the vitreous body. It is enclosed within a lens capsule and it constitutes part of the refracting mechanism of the eye. The structure of the tissue in the lens includes a lens nucleus which is surrounded by the lens cortex. More specifically, the lens cortex includes separate envelope-like layers of tissue which completely surround the nucleus and all other layers which are located closer to the nucleus. The result is that the lens, in cross section, exhibits an anatomy that structurally appears somewhat like an onion.

As recognized by the present invention, the use of a laser beam to make a plurality of minute incisions throughout the cataractous lens tissue will accomplish at least two results that facilitate the removal of the tissue from the lens capsule. Firstly, such incisions assist in mechanically separating the cataractous lens tissue into small particles. Secondly, the vapors which are released during the photoablation of the incisions will infiltrate between the layers of the lens and will act to liquify the lens tissue. Together, the mechanical separation of the tissue and the tissue liquification process which results from photoablation, appropriately alter the cataractous tissue so that it can be aspirated from the lens capsule.

In light of the above it is an object of the present invention to provide a device for generating a laser beam to create a plurality of minute incisions throughout cataractous tissue of an eye to separate and liquify the lens tissue prior to removal from the lens capsule. Another object of the present invention is to provide a device for removing cataractous tissue from the lens capsule of an eye by generating a laser beam which is capable of confining photoablation within the confines of the lens capsule. Still another object of the present invention is to provide a device for generating a laser beam which is capable of efficiently using laser energy to photoablate cataractous tissue of an eye. Another object of the present invention is to provide a device for generating a laser beam which is capable of cutting tissue after passing through unfragmented tissue thereby reducing light scattering and improving laser efficiencies. Yet another object of the present invention is to provide a device for removing cataractous tissue from the lens capsule of an eye which is capable of generating a laser beam and continuously referencing the position of each incision into the cataractous lens tissue. Another object of the present invention is to provide a device for generating a laser beam to remove cataractous tissue from the lens capsule of an eye which is relatively simple to use and which is comparatively cost effective.

SUMMARY OF THE INVENTION

The present invention pertains to a device for removing cataractous tissue from the lens capsule of an eye. Essentially, the device is used in a two phase procedure wherein the cataractous tissue in the lens capsule is first liquified, and then the liquified tissue is aspirated. According to the present invention, the liquification of the cataractous lens tissue is accomplished using a cutting laser beam generated by the device of the present invention.

In the device of the present invention, an ophthalmic laser apparatus is used which focuses a cutting laser beam onto an easily observable reference. Specifically, the reference onto which the cutting laser beam is focused is the cross-over point of a double He-Ne guiding beam. Both the cutting laser and the He-Ne guiding beam laser are connected to a computer included in the present invention. With this arrangement, the operator manually positions the double He-Ne guiding beams of the device as desired, and then the computer automatically exposes the focal point of the cutting laser beam onto the cross-over point of the guiding beams. The focal point of the cutting laser is controlled by the computer and is automatically moved in a predetermined manner and along a predetermined path to create an incision into the lens tissue. Each incision is made in a direction from a posterior to an anterior position. By repeating this procedure, the operator selectively makes a plurality of incisions into the cataractous tissue with the cutting laser beam. The vapors which result from these incisions are then allowed to infiltrate between the layers of the lens tissue to further fragment and liquify the tissue. How the incisions are positioned by the computer throughout the cataractous tissue, and the dimensional characteristics of the incision are important for the present invention.

To accomplish the liquification of the cataractous tissue the device of the present invention makes incisions in strata through the lens tissue. More specifically, these various strata can be envisioned as being stacked on top of each other in a posterior-anterior direction. Each stratum includes a plurality of minute incisions having predetermined computer controlled dimensions. Each incision in each stratum is made in a direction from a posterior to an anterior position. The first stratum to be treated is the most posterior of the strata and successively more anterior stratum are then treated until all of the cataractous tissue in the lens capsule has been treated.

The first, most posterior, stratum of incisions is created by manually aiming the cross-over of the double He-Ne guiding beam onto the posterior capsule of the eye. Once the cross-over is so positioned, the operator activates the device. Upon activation, the computer evaluates the orientation of the guide beams and calculates the crossover location. Knowing the location of the cross-over point, the computer uses this as the first reference location and the computer automatically withdraws the guiding beam cross-over approximately 100 um into the lens tissue. This locates the double He-Ne cross-over inside the lens tissue adjacent the posterior capsule of the eye. The computer then automatically positions the focal point of the cutting laser at the cross-over, and the operator triggers the apparatus to make an incision. These steps are repeated as desired by the operator until a strata of incisions have been made adjacent the posterior capsule. It happens that, as the treated tissue liquifies during this process, the refractive characteristics of the treated tissue are changed. This allows the previously liquified stratum to be subsequently used by the operator for referencing the double He-Ne guiding beam.

Subsequent, more anterior, strata are created by manually referencing the double He-Ne guiding beam from the previously liquified lens tissue. As before, after the operator has positioned the cross-over, the computer positions the focal point of the cutting beam and an incision can be made. Unlike the procedure for the most posterior stratum, however, there is no further need to withdraw the cross-over before making the incision. Accordingly, the operator indicates to the computer that the present incision is not in the most posterior stratum and the computer knows the pull back from the cross-over point is not required. Following this procedure, the operator again makes a sufficient number of incisions to create a whole stratum of incisions. Each incision in each stratum is made in a direction from a posterior to an anterior position. Additional strata are then created until all of the cataractous tissue in the lens capsule has been liquified.

The device of the present invention, knowing the starting point of the respective incisions, is able to make each individual incision by moving the focal point of the cutting laser beam along a path which begins at the previously determined start point creating an incision that is approximately two millimeters (2 mm) in length and approximately five hundred microns (500 um) in depth. Further, in order to provide additional protection for the posterior capsule and the anterior capsule from the incisions, the incisions can be curved automatically by the computer. Moreover, the computer can be programmed so that the radius of curvature of the incisions is varied from stratum to stratum. Specifically, these variations are typically made to transition from an anterior concave curve for incisions in the most posterior stratum, through substantially uncurved incisions in the stratum along the equator of the lens, to an anterior convex curve for incisions in the most anterior stratum. Typically, the computer controlled cutting beam provides incisions in the most posterior stratum which have an anterior oriented radius of curvature of approximately six millimeters (6 mm), while the incisions in the most anterior stratum have a posterior oriented radius of curvature of approximately six millimeters (6 mm). The computer and the controlling mechanism of the cutting beam are such that the operator can use default settings of length, depth and curvature, or the operator can input specific settings for specific applications.

In addition to allowing changes in the curvature, depth and length of the incisions, the laser energy used to make the incisions can be varied from stratum to stratum. Normally, each incision in the most posterior stratum is made using a cutting laser beam having approximately four hundred microjoules (400 uj) of laser energy at its focal point. This level of laser energy for the cutting laser beam is then reduced by approximately seventy-five microjoules (75 uj) for the creation of each successive more anterior stratum of incisions. This reduction in energy can be automatically provided by the computer when switching strata, or the operator can adjust the energy manually.

The novel features of this invention, as well as the invention itself, both as to its structure and its operation will be best understood from the accompanying drawings, taken in conjunction with the accompanying description, in which similar reference characters refer to similar parts, and in which:

BRIEF DESCRIPTION OF THE DRAWINGS

FIG. 5A is a perspective view of the contained volume of an incision in a posterior stratum;

FIG. 5B is a perspective view of the contained volume of an incision in the equatorial stratum;

FIG. 5C is a perspective view of the contained volume of an incision in an anterior stratum;

FIG. 6 is a cross sectional view of the lens of an eye as seen in FIG. 1 with a liquified posterior layer of cataractous lens tissue; and FIG. 7 is a cross sectional view of the lens of an eye as seen in FIG. 6 with substantially all of the cataractous lens tissue liquified for aspiration.

DESCRIPTION OF THE PREFERRED EMBODIMENTS

Figure 1:
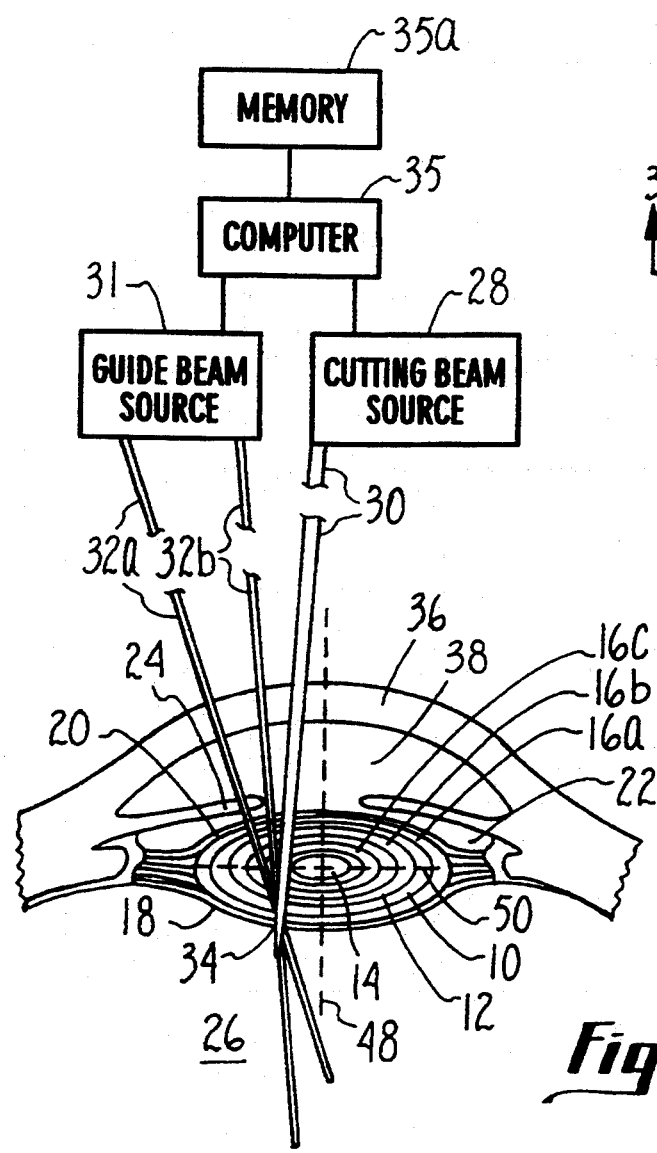
FIG. 1 is a cross sectional view of the lens of an eye, together with its associated anatomy, and a schematic presentation of a laser apparatus operatively positioned in front of the eye.

Referring initially to FIG. 1, a portion of the eye is shown with the lens of the eye designated 10. It is known that the lens 10 includes a cortex 12 which surrounds a nucleus 14, and that both the cortex 12 and nucleus 14 comprise a crystalline tissue. Further, it is known that the cortex 12 is actually a plurality of layers 16 of crystalline lens tissue, of which the designated layers 16 a–c are representative. More specifically, each of the layers 16 completely surround both the cortex 12 and any of the other layers 16 that are located between that particular layer 16 and the cortex 12. The tissue structure of the lens 10 is, therefore, somewhat like that of an onion. FIG. 1 shows that lens 10 is enclosed within a lens capsule which has a posterior capsule 18 and an anterior capsule 20, and that lens 10 is located behind both the posterior chamber 22 and iris 24 of the eye, and in front of the vitreous body 26.

The device of the present invention incorporates a cutting beam laser source 28 to generate a cutting laser beam 30. Although several different laser systems can be used to generate the cutting laser beam 30, it is preferable that the laser source 28 be capable of generating pulsed laser beams similar to those disclosed in U.S. Pat. No. 4,764,930 which issued to Bille et al. and is assigned to the same assignee as the present invention. The disclosure of U.S. Pat. No. 4,764,930 is incorporated herein by reference. Additionally, the device of the present invention includes a guide beam laser source 31 which is capable of generating what is commonly referred to as a double He-Ne laser guide beam 32. The double He-Ne (Helium and Neon) emits light in the visible range. Thus, when the two separate beams 32a and 32b of the double He-Ne are angled with respect to each other, a reflection of their cross-over point 34 can be observed. As those skilled in the art will appreciate, the use of a guide beam other than a He-Ne beam for guide beam purposes would not depart from the scope of the present invention. For purposes of the present disclosure, a number of different types of focal point guide systems could replace the He-Ne guide beam system without departing from the scope of the present invention. Generally, the cutting laser beam 30 is focused so that its focal point is coincident with the cross-over 34 of the double He-Ne beam 32. This arrangement allows use of the cross-over 34 to guide the positioning and location of the focal point of the cutting beam 30.

More specifically, the guide beams 32 are manually adjustable by the operator to position the cross-over point 34. A computer 35, including a memory 35a, is connected to the guide beam generator 31 and the cutting beam generator 28. Computer 35 is well known in the industry and is capable of monitoring the orientation of the beam emitters in the guide beam source 31, and is thereby able to determine the location of the cross-over point 34. Additionally, computer 35 is capable of controlling the location of the focal point of the cutting beam 30. For operation of the device of the present invention, suitable software is located in the memory 35a of the computer 35.

The intent of the present invention is, of course, to properly position and move the focal point of the cutting laser 30 through selected portions of the cataractous tissue of lens 10 to vaporize and liquify this tissue for subsequent aspiration. How this is done is crucial because, it is extremely important that all photoablation occur within the lens 10 itself. For example, there could be grave consequences if the posterior capsule 18 were to be inadvertently perforated. Accordingly, the device of the present invention is further described in terms of its operation.

OPERATION

Figure 2:
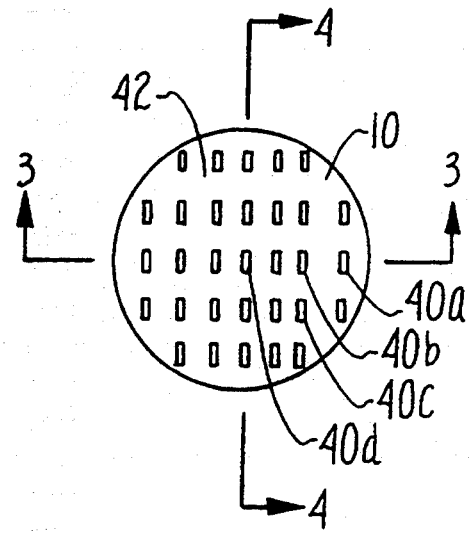
FIG. 2 is a schematic of the lens as would be seen looking along the axis of the eye at the equatorial plane of the lens.

Referring to FIGS. 1 and 2, to begin the procedure incorporating the device of the present invention, the operator first manually locates the cross-over 34 of the double He-Ne beam 32 on the posterior capsule 18 of the eye. The location of the cross-over 34 is determined by the computer and the cross-over 34 is then withdrawn in an anterior direction, i.e. from the posterior capsule 18 toward the anterior capsule 20 and cornea 36 of the eye. Specifically, the cross-over 34 is withdrawn approximately one hundred microns (100 um). This will position the cross-over 34 within the cortex 12 of lens 10 and adjacent the posterior capsule 18. The operator then manually activates the laser source 28 to make an incision 40 into the tissue of lens 10 beginning at the posterior capsule 18 and incising to an anterior position 20. Alternatively, the computer can be programmed to automatically make the incision after withdrawal of the cross-over or to make the incision without the withdrawal of the cross-over point. It is preferred that the cross-over be withdrawn and that the computer pause prior to making the incision thereby allowing the operator to evaluate the incision position and cancel the incision if necessary. This process is repeated until a stratum 42 of minute incisions 40 has been made adjacent the posterior capsule 18.

It happens that the photoablation process which results from using the high intensity, low energy pulsed beam described above not only creates the incisions 40, but also generates vapors that infiltrate between the layers 16 of the cortex 12. These vapors, together with some possible consequent enzyme activity, liquify the tissue in lens 10 along the stratum 42. One consequence of this is that the refractive characteristics of the now liquified tissue are different from the as-yet untreated tissue. The operator can therefore use the stratum 42 as a reference from which to generate additional, more anterior, strata 42. Perhaps this can be better appreciated by a brief reference to FIG. 6 wherein the most posterior strata 42' is shown. The liquified tissue 64 in this strata 42' is what can be used to reference the next more anterior stratum 42 of incisions 40.

FIG. 2 shows a stratum 42 of incisions 40 as might be created by the operator. This stratum 42 is only representative, and the various incisions might well be positioned closer to each other. Further, the incisions 40 need not necessarily be created in neatly aligned rows. It is important, however, that the most posterior stratum 42 be created in reference to the posterior capsule 18 with a withdrawal offset for safety reasons. Subsequent strata 42 are identified to the computer as such and can then be created with reference to previously created stratum 42. More specifically, the cross-over is fixed on the stratum 42 previously created, and the computer, having been informed that the present strata is not the most anterior strata, will position the incisions of the present strata without any withdrawal of the crossover prior to incision. Each subsequent incision in each stratum is made in the direction from a posterior to an anterior position to ensure that the tissue between the cutting beam source 28 and the focal point is unfragmented.

Figure 3:
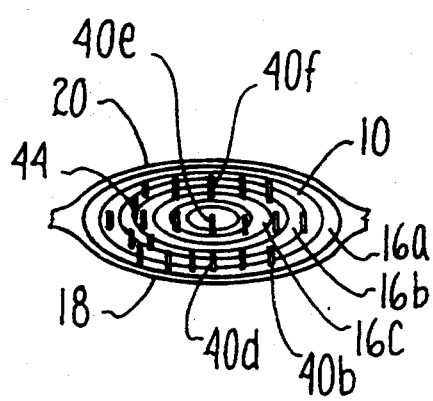
FIG. 3 is a cross sectional view of a lens as seen along the line 3—3 in FIG. 2.
Figure 4:
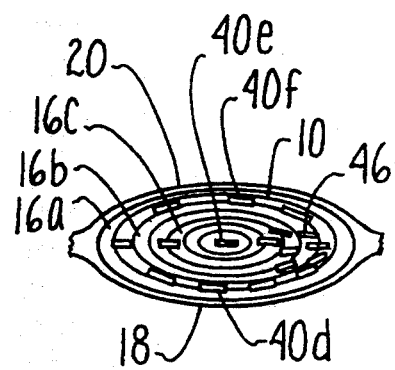
FIG. 4 is a cross sectional view of a lens as seen along the line 4—4 in FIG. 2.

FIGS. 3 and 4 together show perpendicular cross sectional views of the lens 10 with several strata 42 of incisions 40. Again, the location and relationships of the various incisions 40 and the strata 42 are only representative. The cluster 44 of incisions 40 in FIG. 3 and the cluster 46 of incisions 40 in FIG. 4 are, perhaps, more realistic. The separation between the strata 42 and the other incisions 40 is shown for clarity.

In order to better appreciate the orientation of the strata 42 and the dimensional characteristics of the incisions 40 which create the various strata 42, consider the three incisions 40d, 40e and 40f. These three incisions 40 are substantially oriented along the axis 48 of the eye, with the incision 40e located on the equator 50 of the eye. As so arranged, the incision 40d will be in the most posterior stratum 42, the incision 40e will be in the equatorial stratum 42, and the incision 40f will be in the most anterior stratum 42. As before, these are representative strata, and there will most likely be additional strata created between the most posterior and the most anterior strata.

Though, as shown in FIGS. 5A, 5B and 5C, the individual incisions 40 will have slightly different shapes for specific reasons, their dimensions have some commonality. For example, consider the contained volume of the typical incision 40e shown in FIG. 5B. The incision 40e has a length 52 which is approximately two millimeters (2 mm) and a depth or height 54 which is approximately five hundred microns (500 um). The width 56 of the incision 40e will be only a few microns. These same values will be used for corresponding dimensions in the incisions 40d and 40f. As can be appreciated by those skilled in the art, it may be desirable to vary the length and depth of the incisions depending on the situation. For this reason, in addition to having a pre-set default length and width similar to those described above, the computer allows inputting of alternative incision dimensions to over-ride the dimensions recommended by the computer.

FIGS. 5A and 5C show that the incisions 40 can be curved. More specifically, the incision 40d is shown in FIG. 5A with a radius of curvature 58 which is approximately six millimeters (6 mm). Importantly, since the incision 40d is representative of the incisions 40 in the most posterior stratum 42', the radius of curvature 58 is oriented anteriorly from the incision 40d. Thus, incision 40d is curved in a direction which conforms the convex surface of incision 40d with the posterior capsule 18 of the eye. On the other hand, but similarly, since the incision 40f is in the most anterior stratum 42, it is shown in FIG. 5C to be curved with a radius of curvature 60 that is oriented posteriorly from the incision 40f. Thus, incision 40f is curved in a direction which conforms its convex surface with the anterior capsule 20 of the eye. The incision 40e, shown in FIG. 5B has no curvature, and any incisions 40 which are between the stratum 42 of incisions 40e and the respective stratum 42 of incision 40d or 40f can have intermediate curvatures. Computer 35 is capable of allowing the operator to input the curvature of the posterior capsule 18 and the anterior capsule 20 by identifying a finite set of locations on their respective surfaces. These points are located by positioning the cross-over point on their surfaces and having the computer determine the location of the respective points. Once the computer is apprised of a set of points corresponding to the capsule surfaces, the computer can determine the approximate curvature of the capsules. This same of set data points can be used to determine the distance between the posterior and anterior capsules. Having determined the curvatures of the capsules, and the distance between the capsules, the computer can determine the optimum number of strata and incisions as well as the dimensions and curvatures of the strata. These computer determined incisions can be automatically performed by the device, although for purposes of safety, it is preferred that the computer recommend to the operator the locations and specifications of the incisions, and that the incisions are approved by the operator prior to performance of the incisions.

Whereas the selection of the location in the tissue of lens 10 where an incision 40 is to be made can be done manually or automatically as described above, the actual incision 40 is done automatically. For example, for each incision, the cross-over 34 is located at a point in the tissue of lens 10 as disclosed above. This will establish a start point 62, such as the start point 62 shown for incision 40d in FIG. 5A. Laser source 28, controlled by computer 35 directs cutting beam 30 to photoablate a volume of tissue, such as the volume represented by the incision 40d in FIG. 5A. It is to be appreciated that the particular start point 62 can be varied relative to the incision 40 according to the desires of the operator and preprogrammed instructions. As examples, the start points 62' and 62'' are respectively shown for the incisions 40e and 40f.

Due to the fact that less tissue is being crossed by the cutting beam 30 as the more anterior strata 42 are created, the power requirements for the beam 30 can be reduced. For example, the initial power required for photoablating incisions 40 into the most posterior stratum 42' will be approximately four hundred microjoules (400 uj) per pulse. This level of power can be reduced by approximately seventy five microjoules (75 uj) for each more anterior stratum 42. Further, it may be desirable to reduce relative power for incisions 40 near the axis 48 as compared to the more peripheral incisions which are farther away from the axis 48. The power level of the various incisions can be varied manually or automatically by the computer using the curvature and capsule separation data. Preferably, the computer suggests the power level for the incisions along with the other incision recommendations and waits for approval by the operator prior to making the incision. The computer is able to accept both approval for some recommendations and specific inputs for the settings for each incision.

The FIGS. 6 and 7 respectively show a lens 10 which has been partially liquified, and the same lens 10 with substantially all of the cataractous tissue liquified. Once the lens 10 has been treated, the liquified tissue 64 can be removed. To do this, an aspirator 66 is inserted through the sclera 68 and into the lens capsule, through the anterior capsule 20, to aspirate the liquified tissue 64. Typically, a plastic or acrylic lens is then surgically positioned in the capsule to restore sight for the patient. It is possible, with the present invention, that a liquid, rather than a plastic lens, may be used to replace the cataractous tissue 64 which has been removed from the lens capsule. While the above description describes the device in terms of a lentectomy it will be appreciated that the present invention would be equally useful in other surgical procedures.

While the particular method for removing cataractous tissue from the lens capsule of an eye as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

We claim:

1. A device for photoablation of tissue, comprising:
   a cutting laser beam source for generating a cutting laser beam;
   first aiming means for directionally aiming said cutting laser beam along a desired path;
   focussing means for focussing said cutting laser beam at an ablating point at a desired longitudinal position along said path;
   a guide laser beam source for generating first and second guide laser beams;
   second and third aiming means for directionally aiming said first and second guide laser beams, respectively, to intersect at a desired target point to define said target point in three dimensional space at said intersection of said first and second guide laser beams, said second and third aiming means generating directional information defining the respective direction in which each said guide laser beam is aimed; and
   computer means for receiving said directional information from said second and third aiming means, for calculating a three dimensional location of said target point at said intersection of said guide laser beams, and for generating aiming and focussing information as required to control said first aiming means and said focussing means as required to position said ablating point at said three dimensional location of said target point.

2. A device as claimed in claim 1, wherein:
   said computer means further calculates a curvature of a reference tissue surface defined by three dimensional locations of a plurality of reference points on said reference tissue surface, said plurality of reference points being defined by sequentially aiming said guide laser beams to intersect at said plurality of reference points; and
   said computer means controls said first aiming means and said focussing means as required to move said ablating point in a desired pattern to ablate sections of tissue in desired shapes to match said curvature of said reference tissue surface.

3. A device as claimed in claim 1, wherein:
   said computer means further calculates a location of a reference tissue surface defined by three dimensional locations of a plurality of reference points on said reference tissue surface, said plurality of reference points being defined by sequentially aiming said guide laser beams to intersect at said plurality of reference points; and
   said computer means controls said first aiming means and said focussing means as required to position said ablating point to avoid ablating said reference tissue surface.

4. A device as claimed in claim 1, wherein:
   said second and third aiming means allow manual aiming of said guide laser beams by an operator; and
   said intersection of said guide laser beams is visible.

5. A device as claimed in claim 1, wherein said computer means calculates an amount of tissue to be traversed by said cutting laser beam to reach said desired target point, and further comprising means for automatically adjusting a power level of said cutting laser beam according to said amount of tissue to be traversed.

6. A device for photoablation of substantially clear crystalline tissue, comprising:
   a cutting laser beam source for generating a cutting laser beam;
   first aiming means for directionally aiming said cutting laser beam along a desired path;
   focussing means for focussing said cutting laser beam at a desired ablating point at a desired longitudinal position along said path;
   a guide laser beam source for generating first and second guide laser beams;
   second and third aiming means for allowing an operator to manually individually aim said first and second guide laser beams, respectively, to visibly intersect at a desired target point within said tissue to define said target point in three dimensional space at said intersection of said first and second guide laser beams, said second and third aiming means generating directional information defining the respective direction in which each said guide laser beam is aimed; and
   computer means for receiving said directional information from said second and third aiming means, for calculating a three dimensional location of said target point at said intersection of said guide laser beams, and for generating aiming and focussing information as required to control said first aiming means and said focussing means as required to position said ablating point at said three dimensional location of said target point;
   means for adjusting a power level of said cutting laser beam; wherein:
   said computer means further calculates a location and a curvature of first and second reference tissue surfaces defined by three dimensional locations of a plurality of reference points on said reference tissue surfaces, said plurality of reference points being defined by sequentially aiming said guide laser beams to intersect at said plurality of reference points;
   said computer means calculates an amount of tissue to be traversed by said cutting laser beam to reach said desired target point;
   said computer means controls said first aiming means and said focussing means as required to move said ablating point in a desired pattern to ablate sections of tissue in desired shapes to match said curvature of said reference tissue surface;
   said computer means controls said first aiming means and said focussing means as required to position said ablating point to avoid ablating said reference tissue surface; and
   said computer means controls said power adjustment means according to said amount of tissue to be traversed.

7. A method for photoablating tissue, comprising the steps of:
   providing a cutting laser beam source for generating a cutting laser beam which can be aimed along a desired path and focussed at an ablating point along said path;
   providing a guide laser beam source for generating first and second guide laser beams which can be individually aimed as desired by an operator;
   providing a computer means;

individually aiming said first and second guide laser beams, respectively, to visibly intersect at a desired target point within said tissue to define said target point in three dimensional space at said intersection of said first and second guide laser beams;

generating directional information defining the respective direction in which each said guide laser beam is aimed;

receiving said directional information with said computer means;

calculating a three dimensional location of said target point with said computer means;

generating aiming and focussing information as required, with said computer means, to aim and focus said cutting laser beam as required to position said ablating point at said three dimensional location of said target point; and energizing said cutting laser beam source to ablate a desired section of said tissue at said target point.

8. A method as claimed in claim 7, comprising the further steps of:

defining a plurality of reference points on first and second reference tissue surfaces by sequentially aiming said guide laser beams to intersect at said plurality of reference points;

generating directional information defining the respective direction in which each said guide laser beam is aimed, for each said reference point;

receiving said directional information with said computer means;

calculating a three dimensional location of each said reference point with said computer means;

calculating, with said computer means, a location and a curvature of said first and second reference tissue surfaces, using said three dimensional locations of said reference points;

aiming and focussing said cutting laser beam with said computer, as required to move said ablating point in a desired pattern to ablate sections of tissue in desired shapes to match said curvatures of said reference tissue surfaces.

9. A method as claimed in claim 8, comprising the further step of aiming and focussing said cutting laser beam as required to position said ablating point to avoid ablating said reference tissue surfaces.

10. A method as claimed in claim 8, comprising the further steps of:

calculating, with said computer means, an amount of tissue to be traversed by said cutting laser beam to reach said desired target point;

adjusting a power level of said cutting laser beam, with said computer means, according to said amount of tissue to be traversed.

11. A method for photoablating lens tissue in an eye, comprising the steps of:

(a) providing a cutting laser beam source for generating a cutting laser beam which can be aimed along a desired path and focussed at an ablating point along said path;

(b) providing a guide laser beam source for generating first and second guide laser beams which can be individually aimed as desired by an operator;

(c) providing a computer means;

(d) defining a plurality of reference points on the anterior capsule and the posterior capsule of the eye, by sequentially individually aiming said guide laser beams to intersect at said plurality of reference points;

(e) generating directional information defining the respective direction in which each said guide laser beam is aimed, for each said reference point;

(f) receiving said directional information with said computer means;

(g) calculating a three dimensional location of each said reference point with said computer means;

(h) calculating, with said computer means, a location and a curvature of said anterior and posterior capsules, using said three dimensional locations of said reference points;

(i) individually aiming said first and second guide laser beams, respectively, to visibly intersect at a desired target point on the posterior capsule, to define said target point in three dimensional space at said intersection of said first and second guide laser beams;

(j) generating directional information defining the respective direction in which each said guide laser beam is aimed;

(k) receiving said directional information with said computer means;

(l) calculating a three dimensional location of said target point with said computer means;

(m) relocating said target point forwardly, with said computer, to space said target point away from said posterior capsule;

(n) generating aiming and focussing information as required, with said computer means, to aim and focus said cutting laser beam as required to position said ablating point at said three dimensional location of said target point;

(o) energizing said cutting laser beam source and moving said ablating point in a desired pattern to ablate a section of lens tissue in a desired shape to match said curvature of said posterior capsule;

(p) repeatedly performing steps (i) through (o) to ablate and liquefy a first layer of lens material adjacent to the posterior capsule;

(q) individually aiming said first and second guide laser beams, respectively, to visibly intersect at a desired target point on an anterior surface of said first layer to define said target point in three dimensional space at said intersection of said first and second guide laser beams;

(r) repeatedly performing said aiming, focussing, and energizing steps, without performing said step of relocating said target points forwardly, to ablate and liquefy second and successive layers of lens material;

(s) shaping said ablated sections in the anterior portion of said lens to match said curvature of said anterior capsule.

* * * * *